(12) United States Patent
Gerner et al.

(10) Patent No.: US 6,837,992 B2
(45) Date of Patent: Jan. 4, 2005

(54) INTEGRATED APPARATUS FOR DEGASSING AND BLENDING MULTIPLE MOBILE PHASE STREAMS

(75) Inventors: Yuri Gerner, Mendota Heights, MN (US); Carl W. Sims, St. Paul, MN (US); Thomas Thielen, Plymouth, MN (US)

(73) Assignee: Systec Inc., New Brighton, MN (US)

( * ) Notice: Subject to any disclaimer, the term of this patent is extended or adjusted under 35 U.S.C. 154(b) by 169 days.

(21) Appl. No.: 10/355,323

(22) Filed: Jan. 31, 2003

(65) Prior Publication Data

US 2004/0016689 A1 Jan. 29, 2004

Related U.S. Application Data

(63) Continuation-in-part of application No. 09/901,824, filed on Jul. 10, 2001, now Pat. No. 6,673,835.

(51) Int. Cl.[7] .............................................. B01D 15/08
(52) U.S. Cl. ..................... 210/198.2; 210/188; 210/656; 138/26; 138/30; 95/46; 96/6; 96/10
(58) Field of Search ............................ 138/28, 26, 30, 138/DIG. 11; 95/46; 96/6, 8, 10; 210/656, 188, 198.2

(56) References Cited

U.S. PATENT DOCUMENTS

| | | | |
|---|---|---|---|
| 2,212,281 A | | 8/1940 | Ullstrand |
| 2,315,179 A | | 3/1943 | Allender |
| 2,407,276 A | * | 9/1946 | Hendel et al. ................. 138/26 |
| 3,348,578 A | * | 10/1967 | Mercier ........................ 138/30 |
| 3,742,727 A | | 7/1973 | Kaiser |
| 3,782,418 A | | 1/1974 | Zahid |
| 4,064,911 A | | 12/1977 | Albrecht |
| 4,088,154 A | * | 5/1978 | Patton et al. ................. 138/30 |
| 4,234,427 A | | 11/1980 | Boehme |
| 4,281,687 A | | 8/1981 | Hutchins et al. |
| 4,299,253 A | * | 11/1981 | Burton ......................... 138/30 |
| 4,325,715 A | * | 4/1982 | Bowman et al. ................. 96/6 |
| 4,523,612 A | * | 6/1985 | Kuklo ........................... 138/30 |
| 4,548,240 A | | 10/1985 | Graham |
| 4,548,713 A | | 10/1985 | Schmid |
| 4,552,182 A | | 11/1985 | Graham |
| 4,729,773 A | * | 3/1988 | Shirato et al. .................... 96/6 |
| 4,986,837 A | * | 1/1991 | Shibata ........................... 96/6 |
| 5,111,848 A | | 5/1992 | Inukai |
| 5,425,803 A | * | 6/1995 | van Schravendijk et al. ... 95/46 |
| 5,762,684 A | * | 6/1998 | Hayashi et al. ................. 95/24 |
| 5,862,832 A | | 1/1999 | Victor et al. |
| 5,980,742 A | * | 11/1999 | Saitoh ....................... 210/198.2 |
| 6,029,711 A | * | 2/2000 | Koch et al. .................. 138/118 |
| 6,039,078 A | | 3/2000 | Tamari |
| 6,063,275 A | | 5/2000 | Traylor |
| 6,076,557 A | | 6/2000 | Carney |
| 6,085,796 A | | 7/2000 | Riga |
| 6,123,108 A | | 9/2000 | Chen et al. |
| 6,248,157 B1 | * | 6/2001 | Sims et al. ........................ 96/6 |
| 6,305,421 B1 | * | 10/2001 | Ahrweiler .................... 138/30 |
| 6,309,444 B1 | * | 10/2001 | Sims et al. .................... 95/46 |
| 6,319,398 B1 | * | 11/2001 | Saitoh ....................... 210/198.2 |
| 6,494,938 B2 | * | 12/2002 | Sims et al. ........................ 96/6 |
| 6,675,835 B2 | * | 1/2004 | Gerner et al. ................. 138/30 |

* cited by examiner

*Primary Examiner*—Ernest G. Therkorn
(74) *Attorney, Agent, or Firm*—Haugen Law Firm PLLP

(57) ABSTRACT

An integrated mobile phase degassing and blending apparatus for transport of liquid chromatography fluids therethrough includes a component having a first portion and a second portion, with the first portion defining an enclosed degassing chamber, and the second portion including a mobile phase blending device, wherein the degassing chamber and the mobile phase blending device are operably coupled to one another such that the liquid chromatography fluids pass directly into the blending device from the degassing chamber. In a particular embodiment, the degassing chamber is specifically configured to accommodate multiple distinct flexible degassing tubes.

9 Claims, 4 Drawing Sheets

INTEGRATED APPARATUS FOR DEGASSING AND BLENDING MULTIPLE MOBILE PHASE STREAMS

CROSS-REFERENCE TO RELATED APPLICATION

The present application is a continuation-in-part of our application Ser. No. 09/901,824, filed Jul. 10, 2001, now U.S. Pat. No. 6,675,835 entitled "BURDOIN TUBING IN DEGASSING AND PULSATION DAMPENER APPLICATIONS" and which is assigned to the same assignee as the present application.

FIELD OF THE INVENTION

The present invention relates to vacuum degassing and pulse-dampening systems generally, and more particularly to vacuum degassing, pulse dampening systems for use in liquid chromatography applications having an integrated degassing chamber and mobile phase blending valve apparatus. This invention also relates to methods for degassing and blending multiple mobile phase materials in a single integrated apparatus.

BACKGROUND OF THE INVENTION

A variety of applications exist today involving the use of fluid solvents or reactants, wherein the presence of dissolved gases, particularly air, is undesirable. One example of such an application relates to mobile phases in high performance liquid chromatography, where the presence of even small amounts of dissolved gases can interfere with the accuracy and sensitivity of the results obtained. In some cases, the dissolved gases can form bubbles in the mobile phase, thereby causing measurement error in chromatographic applications. Furthermore, some dissolved gases can cause deleterious effects on the mobile phase as well as the surrounding componentry. Often times, such detrimental effects caused by the dissolved gases is related to the relative concentration of the gases in the mobile phase. To avoid such effects, the gases are typically removed from the mobile phase through a known degassing process.

An additional issue that exists in present liquid chromatography systems involves the necessity of dampening fluid pressure pulsations flowing through respective flow conduits and through respective chromatographic columns, which pulsations result from uneven draw and discharge from positive-displacement fluid pumps, such as reciprocating pumps. In addition, pulsation upstream from the pump results partially from the opening and closing of the individual gradient proportioning valves. The process of opening and closing blending valves occurs in a relatively short period of time. Displacement of the fluid in a short period of time creates very high instantaneous solvent flow rates. This forms local pressure pulsations which change the valve closing/opening speed and thus detrimentally effects the blending valve dynamic range.

To obtain the most accurate chromatographic measurements possible, fluid (mobile phase) flow through the column and the detector should be nearly constant. Thus, in order to obtain a continuous fluid flow at a substantially constant rate, it is desirable to provide the chromatographic system with a pulse-dampener in the fluid flow conduit between the fluid pump and the column/detector.

Fluid pressure pulsations in liquid chromatography systems may also occur upstream from respective fluid pumps, thereby adversely affecting chromatographic operations upstream from the fluid pump. In many applications, the mobile phase transported through the liquid chromatography system is a blend of multiple solvents. In such embodiments, individual solvent reservoirs are operably connected to a blending valve apparatus to blend desired quantities of the distinct solvents into a unitary mobile phase. Solvent may be drawn from the respective reservoirs into the blending valve apparatus by a downstream fluid pump, which pump subsequently delivers the blended mobile phase to the remaining chromatographic components. Because of the pulsation characteristics described above, it is desirable to provide mechanisms for dampening such pulsations between the respective solvent reservoirs and the blending valve apparatus, as well as downstream from the blending valve apparatus. Fluid flow pulsations drawn into the blending valve apparatus have the tendency to decrease the accuracy of the blended mobile phase, such that desired ratios of respective solvents comprising the blend may not be accurate. Further, fluid flow pulsations into the blending apparatus can negatively affect physical componentry in the blending valve apparatus, and may decrease the overall life expectancy thereof. It is therefore desirable to provide a pulse-dampening characteristic to the fluid flow conduits connecting such chromatographic components, and particularly between respective fluid reservoirs and a mobile phase blending apparatus.

A number of pulse-dampening techniques have been implemented to provide such flow-dampening characteristics in liquid chromatography applications. For example, fluid has been routed into expandable chambers, wherein a sudden influx of fluid pressure causes the expandable chamber to correspondingly expand, thereby increasing internal volume and absorbing excess fluid pressure to maintain a relatively constant fluid pressure downstream of the expandable chamber. Such flow-dampening devices, however, can result in non-laminar flow patterns, which may result in detrimental formation of gas bubbles in the bulk of the mobile phase. As described above, such gas bubbles can interfere with accurate chromatographic analysis.

Other proposed systems provide dead volumes in the fluid flow pathways, which volumes are not completely filled in standard flow regimes. Upon fluid flow pulsations, however, the dead volumes accumulate the excess fluid flow, thereby mitigating the flow impact downstream of the dead volumes. As with the expandable chambers, however, the dead volumes may act to promote non-laminar flow in the fluid conduits.

Some applications utilize elliptical or flattened tubes as pulse-dampening fluid conduits. Such pulse-dampening tubes are sufficiently flexible to change in cross-sectional profile when a fluid pulse is directed through the tubes. Typical applications, however, surround the flexible tubing with restraining means for limiting the extent of cross-sectional distention. Such restraining means act against change in cross-sectional profile of the fluid conduits so that the fluid conduits return to an elliptical or flattened profile after the fluid pulse has been dampened. Such restraining means include biasing means, external bodies, and compressible fluids surrounding the fluid conduits.

In addition, the flow-dampening systems proposed to date fail to address the degassing issue in liquid chromatography applications as described above. A particular method of degassing mobile phases includes the use of semi-permeable synthetic polymer resin materials as a fluid conduit material, and the exposure of such a semi-permeable conduit to a reduced pressure or vacuum environment. To perform the degassing, the fluid to be degassed is caused to flow through the conduit in the reduced pressure environment, which allows the dissolved gases to escape from the mobile phase through the semi-permeable conduit walls. By addressing both the degassing functions and the flow-dampening functions in a single apparatus, increased chromatographic efficiency and reduced-sized chromatographic instruments may be achieved.

A further issue in liquid chromatography systems, particularly in systems incorporating multiple mobile phase streams, involves degassing each mobile phase stream between a respective mobile phase reservoir and a blending or proportioning valve for delivery of a mixed mobile phase composition to the fluid pump. Degassing systems available today separately degas each mobile phase stream through various methods, and subsequently deliver each mobile phase stream to a separate blending valve apparatus. Such configurations require multiple distinct degassing units, for example distinct vacuum degassing chambers. The multiplicity of degassing units increases overall size of the system, which correspondingly increases the length of tubing required downstream of the respective degassing chambers, and connecting the respective degassing chambers to a blending valve apparatus. Relatively long transport conduits extending between respective degassing chambers and a blending valve apparatus increases the opportunity for regassing of the mobile phase, wherein gas undesirably enters the respective mobile phase streams through the semi-permeable tubing prior to the blending valve apparatus. In addition, the relatively long mobile phase conduits incorporating multiple distinct degassing units increases overall cost of manufacturing and operating of this system. Moreover, relatively long mobile phase conduits increase the overall fluid flow restriction therethrough, thereby reducing the effectiveness of the fluid pump, as well as potentially causing inaccurate blending of the respective solvents making up the blended mobile phase.

Accordingly, it is a principle object of the present invention to provide a means for simultaneously degassing multiple mobile phase streams in a single degassing apparatus.

Another object of the present invention is to provide an integrated apparatus having a multiple mobile phase stream degassing chamber and a blending valve device incorporated therein.

A further object of the present invention is to provide a fluid pulse-dampening apparatus having degassing capabilities.

A still further object of the present invention is to provide an unrestrained, substantially elliptical flexible tube for dampening flow pulsations and for degassing fluids passing therethrough.

A yet further object of the present invention is to provide substantially elliptical flexible tubes in a single reduced-pressure chamber for degassing multiple distinct fluids passing through the respective tubes, which tubes further act to dampen fluid pulsations passing therethrough.

Another object of the present invention is to provide a flow-dampening degassing apparatus capable of withstanding fluid pulsations of up to about 100 pounds per square inch.

A still further object of the present invention is to provide a fluid pulse-dampening apparatus having fluid degassing capabilities, wherein the apparatus is substantially configured to maintain laminar fluid flow therewithin.

A further object of the present invention is to provide an integrated degassing chamber and blending valve apparatus including a post-blending polishing loop disposed within the singular degassing chamber.

A yet further object of the present invention is to provide an integrated degassing chamber and blending valve apparatus which inhibits or prevents regassing of the mobile phase through the transfer tubing between the respective solvent reservoirs and the blending valve apparatus.

It is another object of the present invention to provide an integrated degassing chamber and blending valve apparatus that minimizes overall transfer tube volume between the degassing chamber and the blending valve apparatus.

SUMMARY OF THE INVENTION

By means of the present invention, an apparatus for degassing fluids passing through multiple semi-permeable tubes in a single degassing chamber is provided. This is achieved by fabricating the tubes from a gas-permeable and liquid-impermeable material such as an amorphous perflourinated copolymer, and winding them in a predefined pattern within the degassing chamber. Through the use of such amorphous perflourinated copolymers, tubes having sufficient flexibility to extend in a cross-sectional direction for fluid flow pulse-dampening characteristics may be fabricated without compromising fluid degassing characteristics. Through such an apparatus, design efficiency of liquid chromatography applications is enhanced by combining flow-dampening and degassing functionality into one apparatus, as described in the present application.

One embodiment of the integrated degassing and blending apparatus of the present invention includes a component having a first portion and a second portion, with the first portion defining an enclosed degassing chamber for degassing mobile phase passing therethrough, the degassing chamber being operably coupled to a vacuum source such that the degassing chamber has a reduced internal pressure. The second portion of the component includes a mobile phase blending device, wherein the degassing chamber and the blending device are operably coupled to one another such that the mobile phase passes directly into the blending device from the degassing chamber. Preferably, the mobile phase is transported through the apparatus within one or more mobile phase tubes, which tubes preferably comprise a gas-permeable, liquid-impermeable material. In a particular embodiment, the tubes comprise an amorphous perflourinated copolymer, and are substantially elliptical, the tubes being sufficiently flexible to expand in a cross-sectional direction upon incursion of a fluid pulsation to thereby increase an inner volume of the tubes and correspondingly reduce fluid pressure therein.

In some embodiments of the invention, the apparatus includes an outlet tube operably coupled to the blending device and disposed downstream therefrom, with the outlet tube extending into the degassing chamber for further degassing of the mobile phase being transported within the outlet tube. Another embodiment of the integrated degassing and blending apparatus of the present invention provides in an enclosed degassing chamber integrally disposed and operably coupled with a blending valve device, with the degassing chamber being specifically configured to operably accommodate multiple distinct degassing tubes respectfully transporting distinct mobile phase streams therethrough. The degassing chamber is preferably operably coupled to a vacuum source to obtain a reduced internal pressure within the degassing chamber, the degassing tubes being gas-permeable, liquid-impermeable, such that the mobile phase is effectively degassed while passing through the degassing chamber. Preferably, such tubes comprise an amorphous perflourinated copolymer, and are substantially elliptical to thereby operably dampen fluid pulsations passing therethrough.

DETAILED DESCRIPTION OF THE PREFERRED EMBODIMENTS

The objects and advantages enumerated above together with other objects, features and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
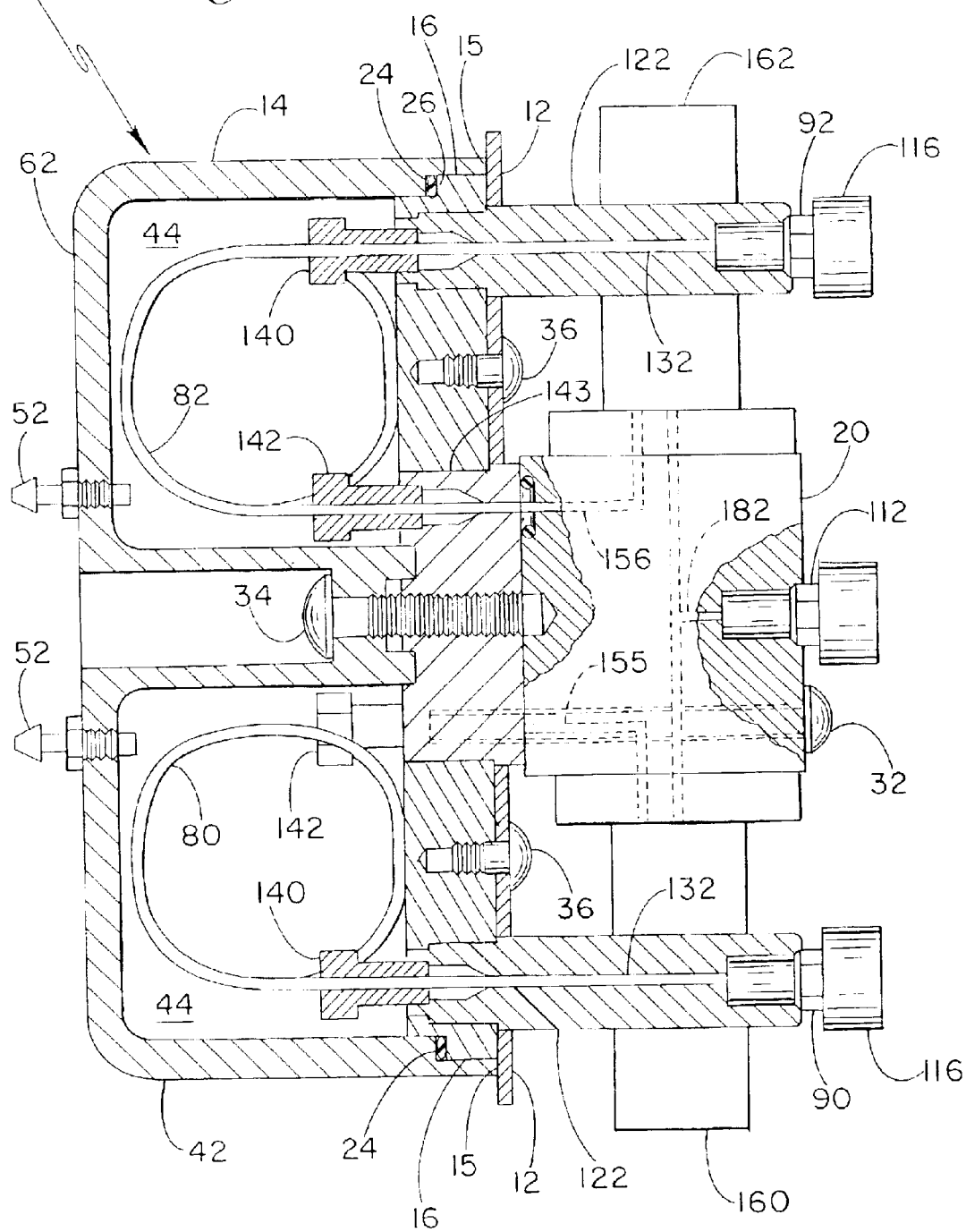
FIG. 1 is a cross-sectional, partial cut-away view of an integrated degassing and blending valve apparatus of the present invention.
Figure 2:
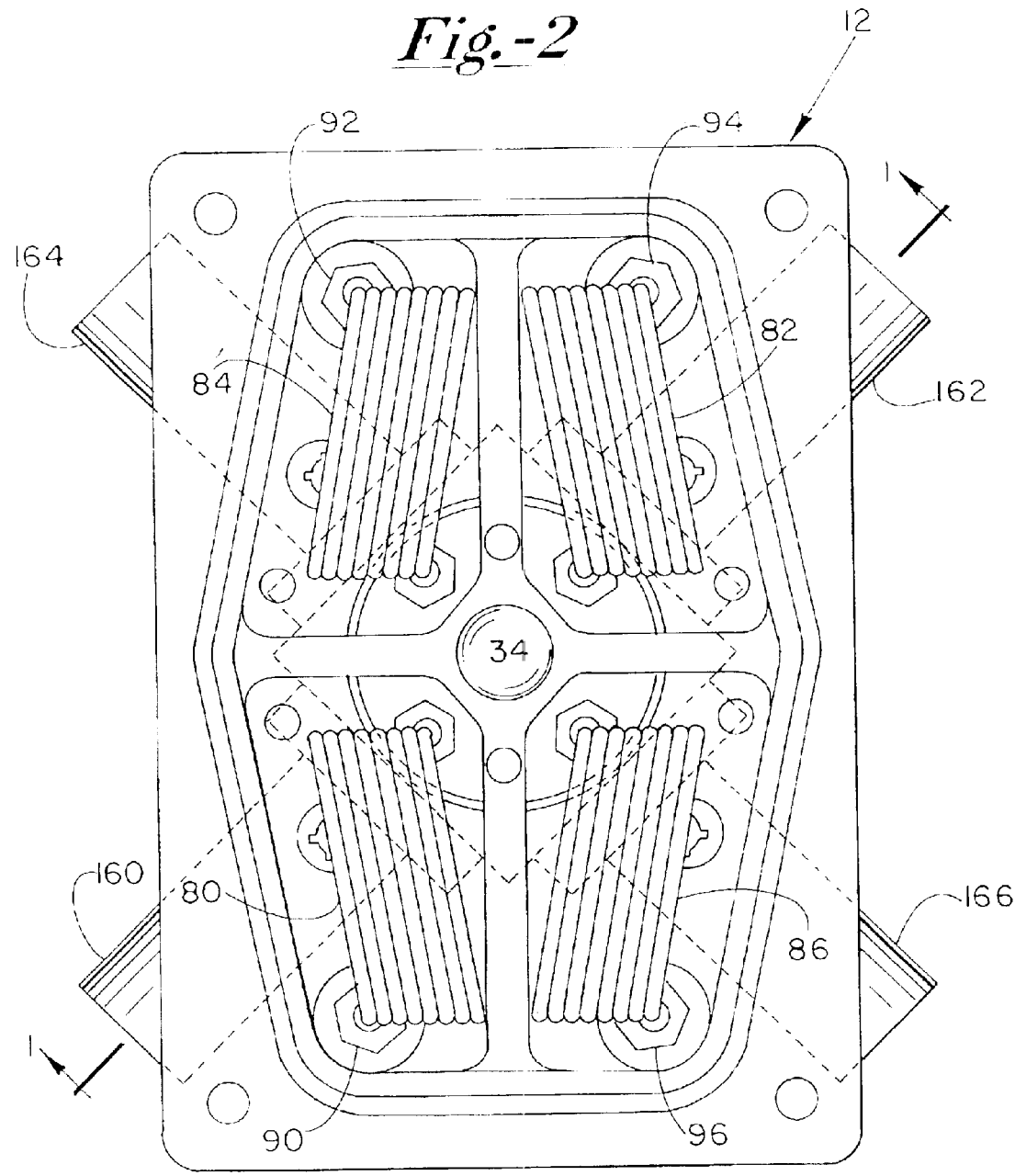
FIG. 2 is a front, partial cut-away view of the integrated degassing and blending valve apparatus illustrated in FIG. 1.

Referring now by characters of reference to the drawings, and first to FIG. 1, a cross sectional view of an integrated degassing/blending valve apparatus 10 of the present invention is shown. FIG. 1 is illustrated in partial cut away view, wherein front mounting plate 12, as shown in FIG. 2, is preferably removably attached to degassing chamber housing 14 via base plate 16. Blending valve unit 20 is also preferably secured to base plate 16 via removable fasteners or the like. Fasteners 32 preferably extend through mounting plate 12 and blending valve unit 20, and into base plate 16 to thereby secure blending valve unit 20 and front mounting plate 12 to base plate 16 and, consequently, to degassing chamber housing 14. When assembled, front mounting plate 12 and degassing chamber housing 14 substaintly form the outer surface of apparatus 10.

In preferred embodiments of the present invention, the degassing chamber housing 14 is a unitary structure being removably engagable to base plate 16 via fasteners 34 or the like. To obtain a desired air-tight seal between degassing chamber housing 14 and base plate 16, one or more resilient O-rings 24 are disposed in an open slot 26 between respective facing portions of the degassing chamber housing 14 and base plate 16. Preferably, base plate 16 is further secured to degassing chamber housing 14 by front mounting plate 12, which plate 12 is secured to base plate 16 via a plurality of fasteners 36. Preferably, front mounting plate 12 extends beyond an outer circumference of base plate 16 to abut against inner end 15 of an outer dimension of degassing chamber housing 14. Such a configuration maintains an airtight seal between degassing chamber housing 14 and the remainder of apparatus 10, whereby degassing chamber 42 can be properly maintained at a negative pressure for mobile phase degassing purposes.

An important aspect of the present invention is in the configuration of the degassing chamber 42, wherein a single airtight chamber under negative pressure produced by a vacuum draw thereupon is capable of simultaneously degassing multiple distinct mobile phase streams. As shown in FIG. 1, degassing chamber housing 14 is configured so as to provide a substantially continuous open space forming a single degassing chamber. Chamber 44 may be annular in configuration, and is preferably a sealed compartment being selectively evacuated via one or more vacuum ports 52 connected thereto. Vacuum ports 52 preferably extend through a rear wall 62 of degassing chamber housing 14 to thereby form a passageway between chamber 44 and the outside of apparatus 10. Preferably, vacuum ports 52 are operably coupled to one or more vacuum pumps (not shown) which operate to selectively evacuate chamber 44 and to thereby provide a negative pressure within chamber 44. The negative pressure developed in chamber 44 is effective in removing gas that permeates from the respective mobile phases through respective degassing tubes 80, 82, 84, 86. The permeated gas is then removed from chamber 44 through respective vacuum ports 52. Mobile phase degassing through respective degassing tubes 80, 82, 84, 86 in chamber 44 is effectuated by Henry's law of partial pressure, wherein gas is drawn from a relatively higher partial pressure to a relatively lower partial pressure.

In preferred embodiments of the present invention, vacuum chamber 42 is preferably manufactured from an impact-resistant polymer material, such as polyethylene, polypropylene, or PPS, which can be readily assembled with sealing o-rings 24 to attach to front mounting plate 12 so as to form a strong, relatively inert exterior shell of the apparatus 10. Degassing chamber housing 14 may also be fabricated from inert metallic material such as aluminum or stainless steel. Front mounting plate 12 is also preferably fabricated from a relatively inert material such as stainless steel, titanium, or polymeric materials.

As can be seen in the figures, respective degassing tubes 80, 82, 84, 86, are preferably wound to form a coil. In such a manner, a relatively large surface area of the respective degassing tubes 80, 82, 84, 86, are exposed to the reduced pressure environment within chamber 44, thereby providing an efficient means for degassing fluids passing through the respective degassing tubes 80, 82, 84, 86. Each respective degassing tube 80, 82, 84, 86 preferably extend between respective inlet connections 90, 92, 94, 96 and a mixed mobile phase outlet connection 112. Negative pressure within chamber 44 is preferably achieved through connection to a vacuum pump (not shown) via vacuum ports 52.

Degassing tubes 80, 82, 84, 86 are preferably fabricated from a semi-permeable polymeric material. In preferred embodiments, degassing tubes 80, 82, 84, 86 are a gas-permeable and liquid-impermeable material such as an amorphous perflourinated copolymer. An example of such an amorphous perflourinated copolymer is Teflon AF™ 2400 manufactured by E. I. dupont de Nemours and Company. Teflon AF™ is a preferred material for use in degassing tubes 80, 82, 84, 86 for its desirable degassing and inertness characteristics.

In some embodiments of the present invention, degassing tubes 80, 82, 84, 86 are substantially burdoin shaped, thereby being larger in a first cross-sectional dimension than in a second cross-sectional dimension. Such a preferred configuration provides a flow-dampening characteristic to degassing tubes 80, 82, 84, 86, wherein tubes 80, 82, 84, 86 are able to expand in a direction along the second cross-sectional dimension, thereby increasing the internal volume of respective tubes 80, 82, 84, 86 upon incursion of the fluid pulsation. By increasing the internal volume within tubes 80, 82, 84, 86, internal fluid pressure is correspondingly decreased and the fluid pulsation thereby dampened. Once the fluid pulsation has been dampened, resiliency in tubes 80, 82, 84, 86 causes the tubes to regain their original, substantially burdoin shaped configuration. Preferably, such flow-dampening degassing tubes 80, 82, 84, 86 have a wall thickness of between about 0.002 inches and about 0.010 inches, though a variety of tube wall thickness may be employed to handle various expected internal fluid pressures and fluid pulsations. In preferred embodiments, however, tubes 80, 82, 84, 86 are each capable of handling and dampening flow pulsations of up to about 100 lbs/in$^2$. If greater wall thickness are utilized in respective tubes 80, 82, 84, 86, however, larger fluid pulsation pressures may be effectively dampened.

FIG. 5 is a cross-sectional end view of the preferred configuration for respective degassing tubes 80, 82, 84, 86. As illustrated in FIG. 5, flow-dampening degassing tubes 80, 82, 84, 86 are preferably substantially burdoin shaped, such that a first cross-sectional dimension is larger than a second cross-sectional dimension. As described herein, such a preferred configuration provides desired flow-dampening characteristics.

The flow-dampening degassing tubes of the present invention preferably simultaneously act to degas fluids flowing therethrough and to dampen fluid flow pulsations. In preferred embodiments, the flow-dampening degassing tubes are disposed in a reduced-pressure vacuum chamber to provide desired degassing functionality. In such a manner, the distinct functions of degassing and flow-dampening, which are important to liquid chromatography applications, may be combined in a single apparatus as in the present invention. By combining such functions, liquid chromatography systems may be fabricated in a more compact and efficient manner.

In use, the flow-dampening degassing apparatus of the present invention degasses fluids passing therethrough and dampens fluid pressure pulsations incurred therein. The flow-dampening degassing tubes preferably conduct fluid driven by a fluid pump, which pump may be positive displacement type fluid pump. Thus, the flow-dampening degassing tubes may be operably coupled to the fluid pump inlet or outlet, or may be disposed remotely from the pump. In particular, the tubes of the present invention are preferably utilized between respective solvent reservoirs and a blending valve apparatus, as well as between the blending valve apparatus and downstream chromatographic components.

In many of such pumps, fluid flow deviations occur on a semi-regular basis. Therefore, fluid flow pulsations are quite typical in such applications. To enhance measurement accuracy in liquid chromatography applications, the flow-dampening degassings tubes are preferably temporarily expandable in a cross-sectional direction to increase the volume within the tubes, and thereby decrease fluid pressure therein. In practice, the fluid pulsation causes the flow-dampening degassing tubes to momentarily expand, which act to dampen such a fluid flow pulse. Once the pulse has been dampened, residual resilient forces in the flow-dampening degassing tube act to reconfigure the tubes in a substantially elliptical configuration, thereby readying the tubes for a subsequent fluid flow pulsation. The net effect of such dampening is to normalize the fluid flow exiting the flow-dampening degassing apparatus so that chromatographic instruments downstream of the flow-dampening degassing apparatus receive a relatively constant flow rate of fluid.

In preferred embodiments of the present invention, respective inlet connections 90, 92, 94, 96 each include a connective nut extending through at least a portion of front mounting plate 12, and into respective bulkhead unions 122. Such bulkhead unions extend through base plate 16 and cap 28 so as to provide a path through which fluid transfer tubes 132 may convey respective mobile phases from respective inlet connections 90, 92, 94, 96, and degassing chamber 42. Respective bulkhead unions 122 are preferably fabricated from PEEK, PPS, or any other chemically inert and strong material. Respective transfer tubes 132 preferably extend through connective nuts 116 and through bulkhead unions 122. Preferably, transfer tubes 132 further extend through receiving nuts 140 and into reduced pressure chamber 44. Receiving nuts 140 are preferably fabricated from a relatively inert and durable material such as Tefzel. Though tubing throughout apparatus 10 is preferably fabricated from an amorphous copolymer such as Teflon AF, respective tubing portions not disposed within chamber 44 may be fabricated from other inert materials such as PTFE for cost-savings purposes.

As shown in FIG. 1, mobile phase within respective degassing tubes 80, 82, 84, 86 exit chamber 44 through exit nuts 142, which exit nuts 142 are similar in materials and structure to receiving nuts 140. Respective degassed mobile phases are then conveyed through respective tubing 155, 156, 157, 158 to individual and distinct solenoid chambers 160, 162, 164, 166. Exit nuts 142 are preferably fitted into interface piece 143, which interface piece 143 is pressed into base plate 16 to thereby secure blending valve unit 20 to apparatus 10. Since interface piece 143 is in direct contact with solvent passing therethrough to the respective solenoid chambers 160, 162, 164, 166, it is preferred that interface piece 143 be fabricated from a chemically inert material such as PEEK or PPS.

Solenoid chambers 160, 162, 164, 166 each include a solenoid valve (not shown) disposed therewithin, which solenoid valve is operably coupled to electronic control devices that are programmable by the user to selectively open and close the respective solenoid valves. In such a manner, the user may remotely program the respective solenoid valves to open for predetermined periods of time, thereby allowing predetermined volumes of selected mobile phase streams within tubing 155, 156, 157, 158 to be passed through their respective solenoid valves and into blending valve unit 20. Blending valve unit 20 operably mixes discrete volumes of distinct mobile phases into a single mobile phase stream within a outlet tube 182. Throughout the fluid flow and fluid blending process, a fluid pump, typically downstream from outlet 112 of apparatus 10, forces the respect mobile phase streams to flow through their respective conduits.

Due to the discrete volume nature of the fluid flow passing through respective solenoid valves, it is an advantageous aspect of the present invention to utilize substantially elliptical tubing downstream of the respective solenoid valves, such that "pulses" of discrete fluid volumes are adequately absorbed by the tubing to substantially normalize mixed mobile phase pressure within outlet tubing 182.

Figure 3:
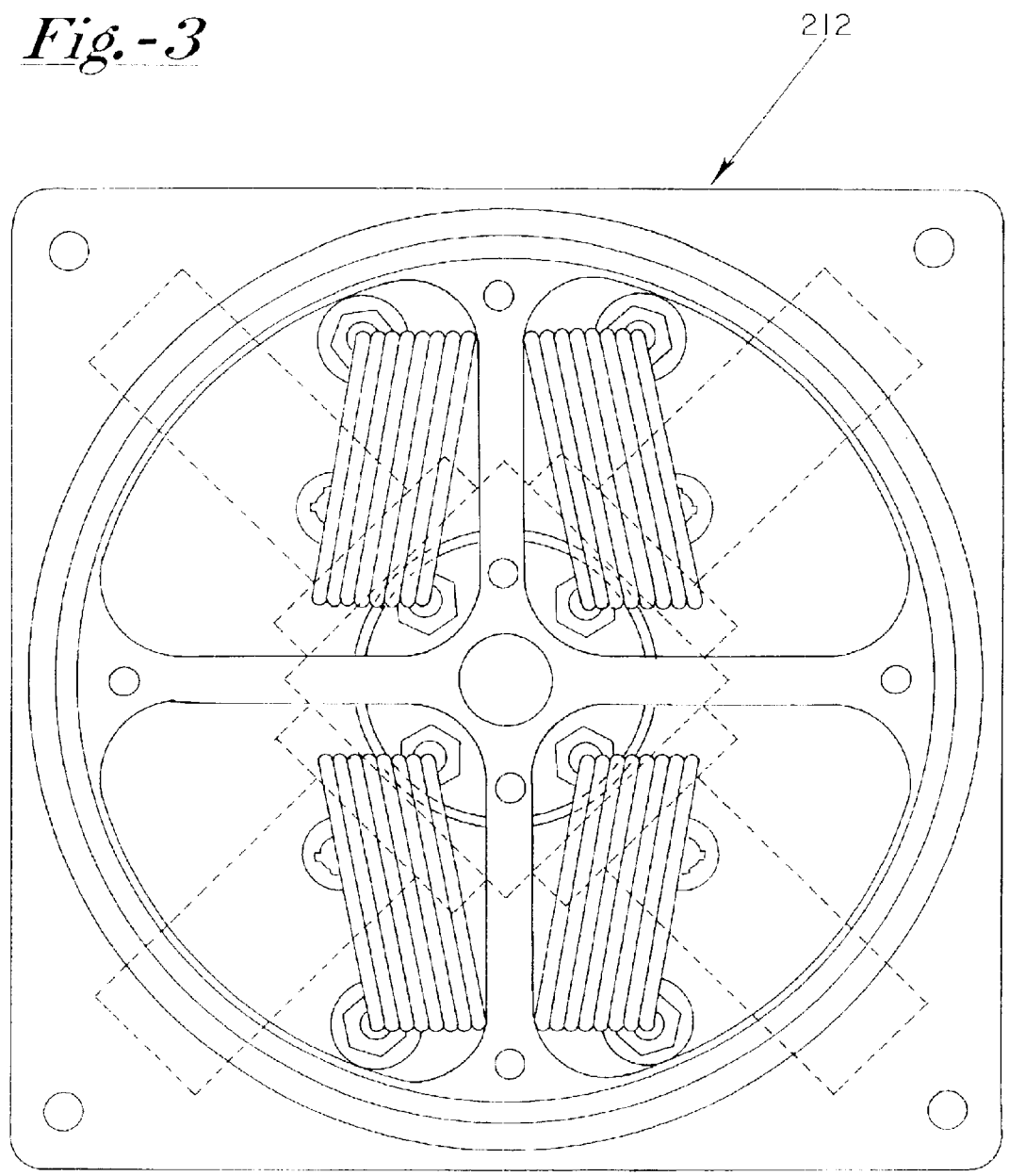
FIG. 3 is a front cut away view of an integrated degassing and blending valve apparatus of the present invention.
Figure 4:
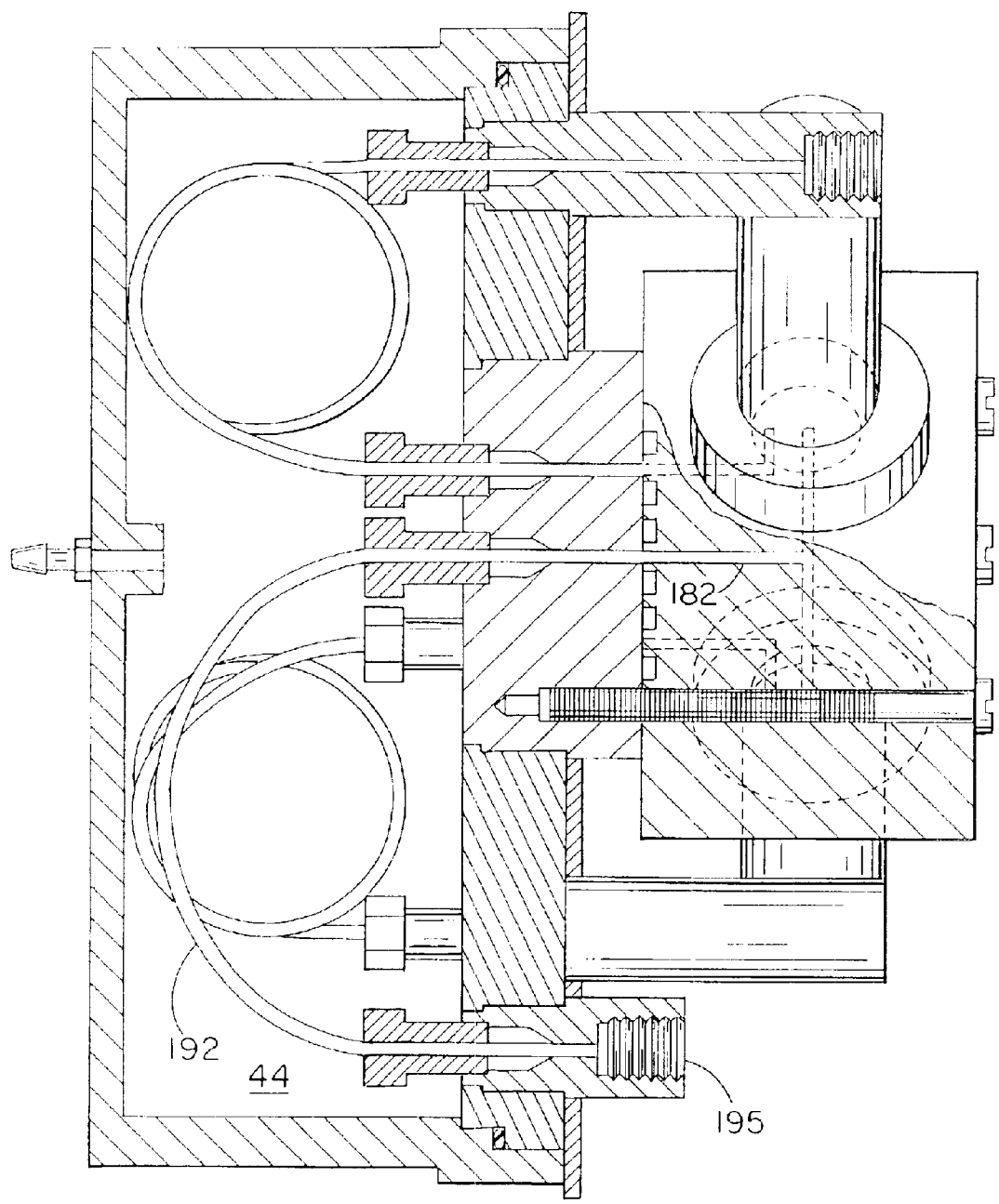
FIG. 4 is a cross-sectional view of an integrated degassing and blending valve apparatus of the present invention.

As illustrated in FIGS. 2 and 3, a variety of mounting plate configurations are contemplated by the present invention for use in various distinct applications. The mounting plate 212 of FIG. 3, for example, is substantially square to accommodate a substantially circular base plate 16 and degassing chamber 42. By contrast, the elongated base plate 12 of FIG. 2 preferably accommodates a more elongated degassing housing 42 and base plate 16. Such variety of configuration provides adaptability to numerous different applications. The configurations illustrated herein are by no means limiting, in that any configuration incorporating the aspects of the present invention are contemplated by the present invention.

In a further aspect of the present invention, as illustrated in FIG. 5, outlet tube 182 may be preferably re-routed back into degassing chamber 44 for degassing mobile phase subsequent to blending operations. Such post-blending degassing further ensures that minimal entrained or dissolved gas is delivered to chromatographic instruments in the mobile phase downstream from degassing apparatus 10. Preferably, such a post-blending degassing procedure is accomplished in a polishing loop 192 of degassing tubing preferably fabricated from an amorphous perflourinated copolymer such as Teflon AF™. In such an embodiment, blended mobile phase exiting polishing loop 192 is directed out from apparatus 10 toward the fluid pump (not shown).

As stated above, a particular aspect of the present invention is to provide a single integrated apparatus incorporating a degassing chamber and a blending valve apparatus. Such an integrated apparatus conserves overall chromatographic apparatus volume as well as minimizes mobile phase travel distance from respective reservoirs to chromatographic instruments. Such minimization of mobile phase travel preferably minimizes entrained or dissolved gases within the mobile phase when the mobile phase reaches the chromatographic instruments.

A further aspect of the present invention provides for a single vacuum chamber accommodating multiple distinct mobile phase streams, both pre and post blending. Such a configuration is both economical and advantageous in that overall size of the degassing apparatus 10 is minimized as well as the total distance of mobile phase travel from a reservoir to respective chromatographic instruments.

The apparatus of the present invention is further enhanced through the utilization of substantially elliptical tubing for normalizing or dampening fluid flow pulsations caused by typical discontinuous fluid flow throughout the system.

Respective components of the apparatus of the present invention, and particularly the housing, cap, bulkheads, and blending valve apparatus may each preferably be injection molded, machined or any combination thereof.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. An integrated mobile phase degassing and blending apparatus, comprising:
a component having a first portion and a second portion, said first portion defining an enclosed degassing chamber for degassing mobile phase passing therethrough, said degassing chamber being operably coupled to a vacuum source such that said degassing chamber has a reduced internal pressure, said second portion of said component including a mobile phase blending device, said degassing chamber and said mobile phase blending device being operably coupled to one another such that the mobile phase passes directly into said blending device from said degassing chamber wherein the mobile phase is transported through a portion of said apparatus within one or more mobile phase tubes.

2. An integrated mobile phase degassing and blending apparatus as in claim 1 wherein said mobile phase tubes comprise a gas-permeable, liquid-impermeable material.

3. An integrated mobile phase degassing and blending apparatus as in claim 2 wherein said mobile phase tubes comprise an amorphous perflourinated copolymer.

4. An integrated mobile phase degassing and blending apparatus as in claim 2, including an outlet tube operably coupled to said blending device and disposed downstream therefrom, said outlet tube extending into said degassing chamber for degassing the mobile phase being transported within said outlet tube.

5. An integrated mobile phase degassing and blending apparatus in claim 1 wherein said mobile phase tubes are substantially elliptical, and are sufficiently flexible to expand in a cross-sectional direction upon incursion of a fluid pulsation to thereby increase an inner volume of said tubes and correspondingly reduce fluid pressure therein.

6. An integrated mobile phase degassing and blending apparatus as in claim 1, wherein said degassing chamber is specifically configured to accommodate multiple distinct mobile phase tubes, each of said mobile phase tubes transporting respective mobile phase streams from respective mobile phase reservoirs.

7. An integrated mobile phase degassing and blending apparatus, comprising:
an enclosed degassing chamber integrally disposed and operably coupled with a blending valve device, said degassing chamber being specifically configured to operably accommodate multiple distinct degassing tubes respectfully transporting distinct mobile phase streams therethrough, said degassing chamber being operably coupled to a vacuum source to obtain a reduced internal pressure within said degassing chamber, said degassing tubes being gas-permeable, liquid-impermeable such that the mobile phase is effectively degassed while passing through said degassing chamber.

8. An integrated apparatus as in claim 7 wherein said degassing tubes compromise an amorphous perflourinated copolymer.

9. An integrated apparatus as in claim 7 wherein said degassing tubes are substantially elliptical, and are sufficiently flexible to expand in a cross-sectional direction upon incursion of a fluid pulsation to thereby increase an inner volume of said tubes and correspondingly reduce fluid pressure therein.

* * * * *